US00PP14117P39

(12) United States Plant Patent
Yomo

(10) Patent No.: US PP14,117 P3
(45) Date of Patent: Sep. 2, 2003

(54) VERBENA PLANT NAMED 'SUNMAREF TP-SAP'

(75) Inventor: Yasunori Yomo, Shiga (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/328,271

(22) Filed: Jun. 17, 1999

(65) Prior Publication Data

US 2002/0059668 P1 May 16, 2002

(51) Int. Cl.[7] ..... A01H 5/00
(52) U.S. Cl. ..... Plt./308
(58) Field of Search ..... Plt./308

(56) References Cited

U.S. PATENT DOCUMENTS

| | | | | |
|---|---|---|---|---|
| PP8,995 | P | 11/1994 | Tachibana et al. | Plt./308 |
| PP9,014 | P | 12/1994 | Tachibana et al. | Plt./308 |
| PP9,059 | P | 2/1995 | Tachibana et al. | Plt./308 |
| PP9,085 | P | 3/1995 | Tachibana et al. | Plt./308 |
| PP9,121 | P | 4/1995 | Tachibana et al. | Plt./308 |
| PP9,411 | P | 12/1995 | Tachibana et al. | Plt./308 |
| PP10,311 | P | 3/1998 | Tachibana | Plt./308 |
| PP10,705 | P | 11/1998 | Tachibana | Plt./308 |
| PP10,743 | P | 1/1999 | Nagase | Plt./308 |
| PP10,755 | P | 1/1999 | Nagase | Plt./308 |
| PP10,801 | P | 2/1999 | Nagase | Plt./308 |

*Primary Examiner*—Bruce R. Campell
*Assistant Examiner*—Anne Marie Grünberg
(74) *Attorney, Agent, or Firm*—Burns, Doane, Swecker & Mathis, L.L.P.

(57) ABSTRACT

Disclosed herein is a verbena plant named 'Sunmaref TP-SAP' having a broad spreading growth habit and long stems. The plant has abundant branching and forms a large number of flowers in clusters with a great profusion of blooms. The blooming period is from April to November and the flowering duration is long with the entire plant remaining in bloom for a considerable period of time. The flower size is medium and the petal color is a strong purplish pink. The plant is highly tolerant to cold, drought, rain and heat, and exhibits high resistance to pests and diseases, particularly to powdery mildew.

2 Drawing Sheets

Botanical/commercial classification: *Verbena calliantha*/Verbena Plant.

Varietal denomination: cv. 'Sunmaref TP-SAP'.

BACKGROUND OF THE VARIETY

The present invention relates to a new and distinct variety of *Verbena calliantha* plant obtained by crossing a wild type of verbena plant *Verbena calliantha* f. rosea (♀) native to Brazil and the 'Rainbow Carpet Red' (♂) variety (non-patented in the United States) and botanically known as Verbena×hybrida Voss.

The verbena is a very popular plant and is used for flower bedding and potting in the summer season. There are only a few varieties of the verbena plant which have a spreading growth habit, much branching, a large number of flowers in clusters and a high resistance to rain, heat, cold, and diseases. Accordingly, this invention was aimed at obtaining a new variety having a spreading growth habit, strong branching, a large number of flowers in clusters, high tolerance to heat, rain, drought and cold, and resistance to diseases and pests combined with a strong purplish pink petal coloration.

Initially, 35 seedlings were obtained from the crossing in March of 1996. One seedling was selected in view of its spreading growth habit and flower color. The seedling was propagated by the use of cuttings. The resulting plants were tested while growing as potted and bedding plants from the spring of 1997 to the autumn of 1998 and the botanical characteristics were compared to those of the 'Flower Carpet Red' variety. As a result, it was concluded that this verbena plant is distinguishable from any other variety, whose existence is known to us, and is uniform and stable in its characteristics. This new variety of verbena plant was named 'Sunmaref TP-SAP'.

In the following description, the color-coding is in accordance with the chart of The Royal Horticultural Society, London, England (R.H.S. Colour Chart). The color chart based on The Japan Color Standard for Horticultural Plants (J.H.S.. Color Chart) is also added for reference.

The female parent used in the obtaining of this new variety 'Sunmaref TP-SAP' was a wild type of verbena (*Verbena calliantha*) native to South Brazil that was introduced to Japan in 1995. This wild type of verbena plant is presently maintained in Japan. The main botanical characteristics of this female parent are as follows:

Plant:
- *Growth habit.*—Slightly erect and spreading.
- *Plant extension.*—100–150 cm.
- *Plant height.*—5–8 cm.

Stem:
- *Diameter.*—1.0–2.0 mm.
- *Anthocyanin pigmentation.*—Present.
- *Branching.*—Medium.
- *Rhizomes.*—Absent.
- *Pubescence.*—Present.
- *Length of internode.*—2.0–5.0 cm.

Leaf:
- *Phyllotaxis.*—Opposite.
- *Shape of blade.*—Narrow lanceolate.
- *Length.*—2.0–4.0 cm.
- *Width.*—1.0–2.0 cm.
- *Depth of incision.*—Deep.
- *Color.*—Dark green (R.H.S. 137A, J.H.S. 3707).
- *Pubescence.*—Sparse.

Flower:
*Facing direction.*—Upward.
*Outward curvature of petal.*—Slightly curved.
*Diameter.*—1.5–2.0 cm.
*Height.*—15–20 mm.
*Color.*—Deep purplish pink (R.H.S. 66C, J.H.S. 9505).
*Color intensity.*—The coloration is evenly presented.
*Overlapping of petals.*—When the flower is fully open, the petals do not overlap to any substantial degree.
*Cluster.*—20–25 mm in length; and 30–40 mm in diameter.
*Calyx.*—1.0 cm in length.
*Anthocyanin pigmentation of calyx limb.*—Present.
*Peduncle.*—1–2 mm in thickness; and 4.0–5.0 cm in length.
*Number of flowers.*—Plentiful (13–15).
*Reproductive organs.*—1 pistil and 4 stamens.
*Flower fragrance.*—Absent.
*Flowering duration.*—Short.

Physiological and ecological characteristics: High resistance to diseases and pests, high tolerance to heat, and moderate tolerance to cold.

The main botanical characteristics of 'Rainbow Carpet Red' pollen parent are as follows:

Plant:
*Growth habit.*—Semi-erect.
*Plant extension.*—25–30 cm.
*Plant height.*—20–25 cm.

Stem:
*Diameter.*—1.7–1.9 mm.
*Anthocyanin pigmentation.*—Absent.
*Branching.*—Medium.
*Rhizomes.*—Absent.
*Pubescence.*—Sparse.
*Length of internode.*—3.0–3.5 cm.

Leaf:
*Phyllotaxis.*—Opposite.
*Shape of blade.*—Cordate.
*Length.*—2.0–2.5 cm.
*Width.*—1.5–2.0 cm.
*Depth of incision.*—Deep.
*Color.*—Dark green (R.H.S. 137B, J.H.S. 3716).
*Pubescence.*—Sparse.

Flower:
*Facing direction.*—Upward.
*Outward curvature of petal.*—Slightly curved.
*Diameter.*—1.2–1.7 cm.
*Height.*—13–15 mm.
*Color.*—Vivid red (R.H.S. 52A, J.H.S. 0106).
*Color intensity.*—The coloration is evenly presented.
*Overlapping of petals.*—When the flower is fully open, the petals do not overlap to any substantial degree.
*Cluster.*—25–30 mm in length and 30–35 mm in diameter.
*Calyx.*—0.5–1.0 cm in length.
*Anthocyanin pigmentation of calyx limb.*—Present.
*Peduncle* —1.7–1.8 mm in thickness and 4.0–6.0 cm in length.
*Number of flowers.*—Few (7–11).
*Reproductive organs.*—1 pistil and 4 stamens.
*Flower fragrance.*—Absent.
*Flowering duration.*—Medium.

Physiological and ecological characteristics: Moderate tolerance to heat, cold, and pests, and low resistance to diseases.

This new variety of verbena plant named 'Sunmaref TP-SAP' was asexually reproduced by the use of cuttings at the Hakusyu Research Center of SUNTORY Ltd., located at 2913-1 Torihara, Hakusyu-cho, Kitakomagun, Yamanashi-ken, Japan, and the homogeneity and stability thereof were confirmed.

SUMMARY OF THE NEW VARIETY

This new variety of verbena plant has a broad spreading growth habit, and forms long stems. The plant has abundant branching and forms a large number of flowers in clusters with a great profusion of blooms. The blooming period is April to November and flowering duration is long with the entire plant remaining in bloom for a considerable period of time. The flower size is medium and the petal color of the flower is strong purplish pink. The plant is highly tolerant to cold, heat, rain and drought and displays a high resistance to pests and diseases, particularly to powdery mildew.

BRIEF DESCRIPTION OF THE PHOTOGRAPHS

DETAILED DESCRIPTION OF THE NEW VARIETY

Figure 1:
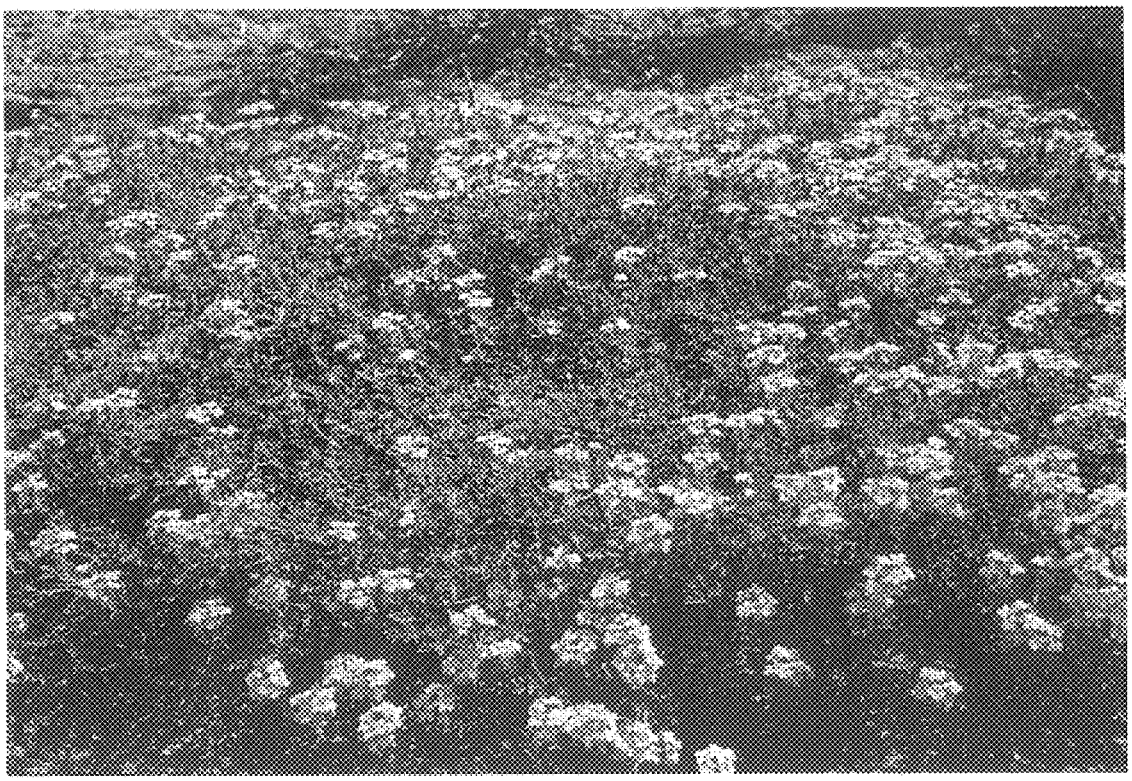
FIG. 1 is photograph giving a partial view of the new variety of verbena plant named 'Sunmaref TP-SAP'.
Figure 2:
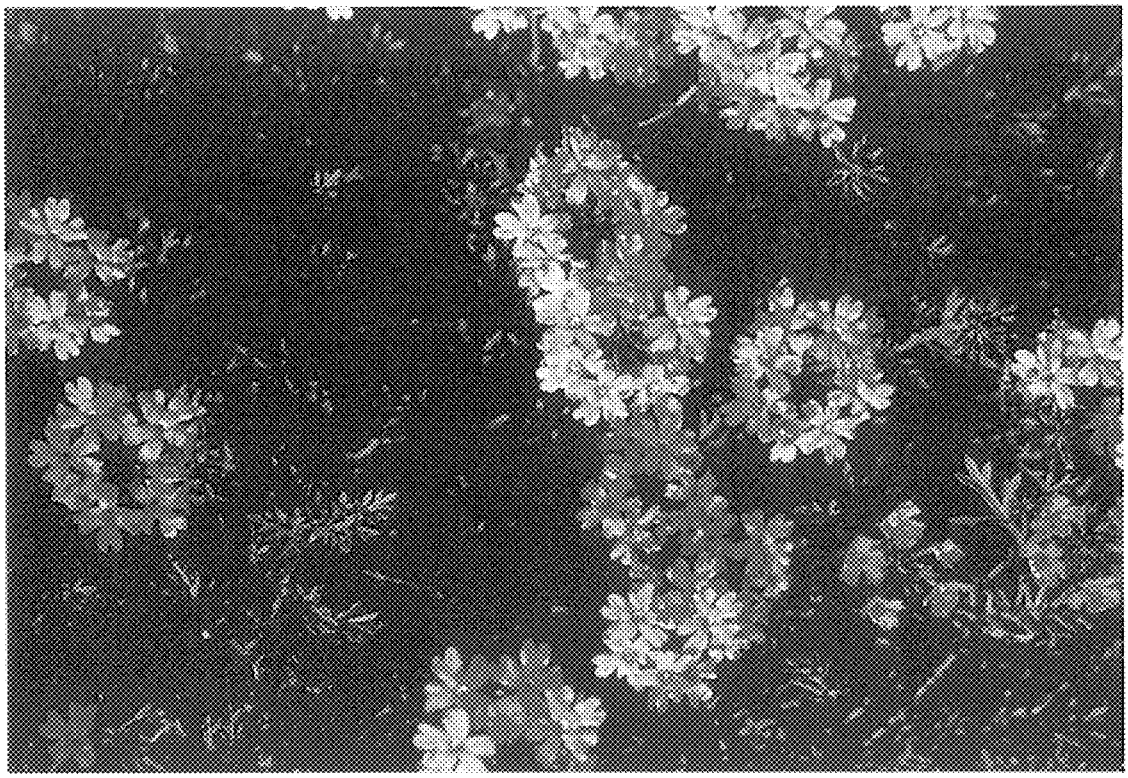
FIG. 2 is a photograph of flowers of the new variety of verbena plant named 'Sunmaref TP-SAP'.

The botanical characteristics of the new and distinct variety of verbena plant named 'Sunmaref TP-SAP' are set forth below. The plants were growing in the field and were observed approximately three months after planting.

Plant:
*Growth habit.*—Spreading.
*Plant extension.*—80–100 cm.
*Plant height.*—10–20 cm.
*Growth.*—Very vigorous with abundant branching and a great profusion of blooms with the entire plant remaining in bloom for considerable period of time.

Stem:
*Diameter.*—2.0–3.0 mm.
*Anthocyanin pigmentation.*—Present.
*Branching.*—Well-branched. Flowers form at the tip of a shoot in a cluster, and as each flower opens two more shoots are formed. Accordingly, the branching increases in this manner.
*Rhizomes.*—Absent. But when the stems contact the surface of soil, the nodes take root in the ground.
*Pubescence.*—Moderate.
*Length of internode.*—2.0–3.0 cm.

Leaf:
*Phyllotaxis.*—Opposite.
*Shape of blade.*—Deltoid base.
*Length.*—3.2–3.6 cm.
*Width.*—1.5–2.2 cm.
*Depth of incision.*—Substantial as illustrated. The deepest sinus commonly is approximately 9 to 10 mm from the leaf margin and the shallowest approximately 2 mm from the leaf margin.
*Color.*—Dark green (R.H.S. 132A, J.H.S. 4307).
*Pubescence.*—Moderate.

Flower:

*Facing direction.*—Upward.

*Petals.*—Typically 5 per bloom, cordate in configuration, approximately 4 to 5 mm in length, and approximately 6 to 7 mm in width.

*Outward curvature of petal.*—Slightly curved.

*Diameter.*—1.3–1.5 cm.

*Height.*—12–14 mm.

*Bud color.*—R.H.S. 67D.

*Color.*—Strong purplish pink (R.H.S. 55A, J.H.S. 9705) on the upper petal surface, and Red-Purple Group 62B on the under petal surface. There is an eye at the center of each corolla having a diameter of approximately 1 mm that is R.H.S. 145B in coloration. Also, there is commonly a small area near the eye having a coloration of R.H.S. 159D.

*Color intensity.*—The coloration is evenly presented.

*Overlapping of petals.*—When the flower is fully open, the petals do not overlap to any substantial degree.

*Cluster.*—30–50 mm in length; and 30–40 mm in diameter.

*Calyx.*—0.7–0.8 cm in length.

*Anthocyanin pigmentation of calyx limb.*—R.H.S. 59C in coloration.

*Peduncle.*—1 mm in thickness; 4.0–5.0 cm in length, and Green Group 137C in coloration.

*Sepals.*—R.H.S. 137C in coloration, five in number, long and narrow, approximately 8 to 9 mm in length, and the surface is scabrous.

*Number of flowers.*—Medium (commonly 7–12 in a cluster).

*Reproductive organs.*—1 pistil having a length of approximately 10 mm and 4 stamens. Two stamens commonly end near the height of the stigma and two stamens commonly extend to a slightly higher level above the stigma. The stamens are R.H.S. 145B in coloration. The stigma is approximately 0.3 mm in size and R.H.S. 144B in coloration. The styles commonly are approximately 0.1 mm in diameter and R.H.S. 145D in coloration.

*Flower fragrance.*—Absent.

*Flowering duration.*—Long, and self-cleaning. Blossoming commonly occurs substantially continuously from spring to autumn. An individual bloom commonly lasts approximately 7 to 10 days depending upon the weather conditions.

*Pollen.*—Sparsely formed and R.H.S. 10C in coloration.

*Fertility.*—Appears to be sterile during observations to date.

Physiological and ecological characteristics: High resistance to diseases and pests, particularly to powdery mildew based on casual greenhouse and field observation. High tolerance to heat, cold, rain and drought.

This new variety of verbena plant is most suitable for flower bedding and potting, particularly in planters, and is further well suited for use as a ground cover.

I claim:

1. A new and distinct variety of verbena plant named 'Sunmaref TP-SAP', substantially as herein illustrated and described, characterized particularly as to novelty by (a) a spreading growth habit with long stems, (b) abundant branching and the formation of a large number of flowers in clusters with a great profusion of blooms, (c) a flower size that is medium and a petal coloration that is strong purplish pink, and (d) a high tolerance to rain, heat, drought, cold, and a high resistance to diseases and pests, particularly to powdery mildew.

* * * * *